United States Patent [19]

Erker

[11] 4,278,889
[45] Jul. 14, 1981

[54] CURRENT AMPLIFIER WITH AUTOMATIC DRIFT CORRECTION FOR TOMOGRAPHIC SCANNERS

[75] Inventor: Joseph W. Erker, Aurora, Ohio
[73] Assignee: Ohio Nuclear, Inc., Solon, Ohio
[21] Appl. No.: 84,777
[22] Filed: Oct. 15, 1979
[51] Int. Cl.³ .............................................. G01T 1/20
[52] U.S. Cl. .............................. 250/445 T; 250/363 S
[58] Field of Search ......................... 250/445 T, 363 S

[56] References Cited

U.S. PATENT DOCUMENTS

| | | | |
|---|---|---|---|
| 3,980,886 | 9/1976 | Stout | 250/363 S |
| 4,068,306 | 1/1978 | Chen et al. | 250/445 T |
| 4,070,581 | 1/1978 | Gibbons et al. | 250/445 T |
| 4,071,760 | 1/1978 | LeMay | 250/445 T |
| 4,114,042 | 9/1978 | LeMay | 250/445 T |
| 4,138,640 | 2/1979 | Cousins | 250/445 T |
| 4,145,610 | 3/1979 | Perilhou | 250/445 T |

OTHER PUBLICATIONS

Harris Semiconductor, *Linear and Data Acquisition Products*, p. 7-70 and p. 7-71.

*Primary Examiner*—Bruce C. Anderson
*Attorney, Agent, or Firm*—Fay & Sharpe

[57] ABSTRACT

The current amplifier with automatic drift correction is designed for use in conjunction with computerized tomographic scanners or other apparatus. The amplifier comprises a differential amplifier with a first input connected to a photodiode or other source of current to be amplified. An integrating amplifier is connected between the differential amplifier output and a second differential amplifier input. The integrating amplifier has a time constant which is long compared with the period during which the diode current is to be amplified to provide automatic drift correction. A feedback loop connects the output of the differential amplifier with the first differential amplifier input. The feedback loop comprises a pair of matched transistors interconnected to form a current mirror. A first resistor connects the current mirror with ground. Current flow through these two resistors is summed to form the current flow received by the current mirror. The mirror current generated by the current mirror forms the amplifier output signal.

15 Claims, 2 Drawing Figures

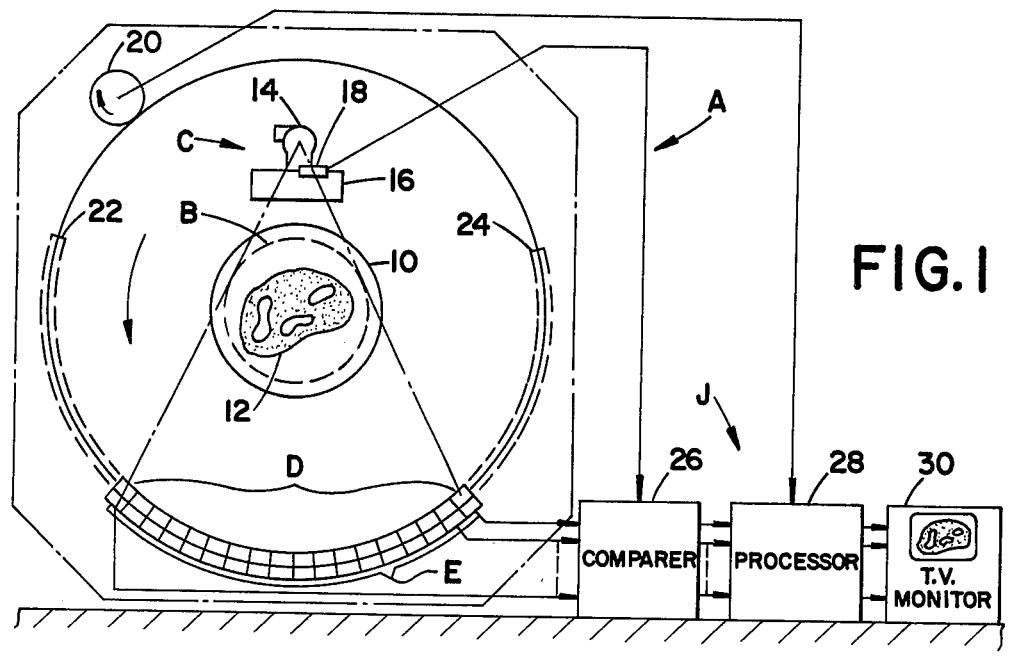
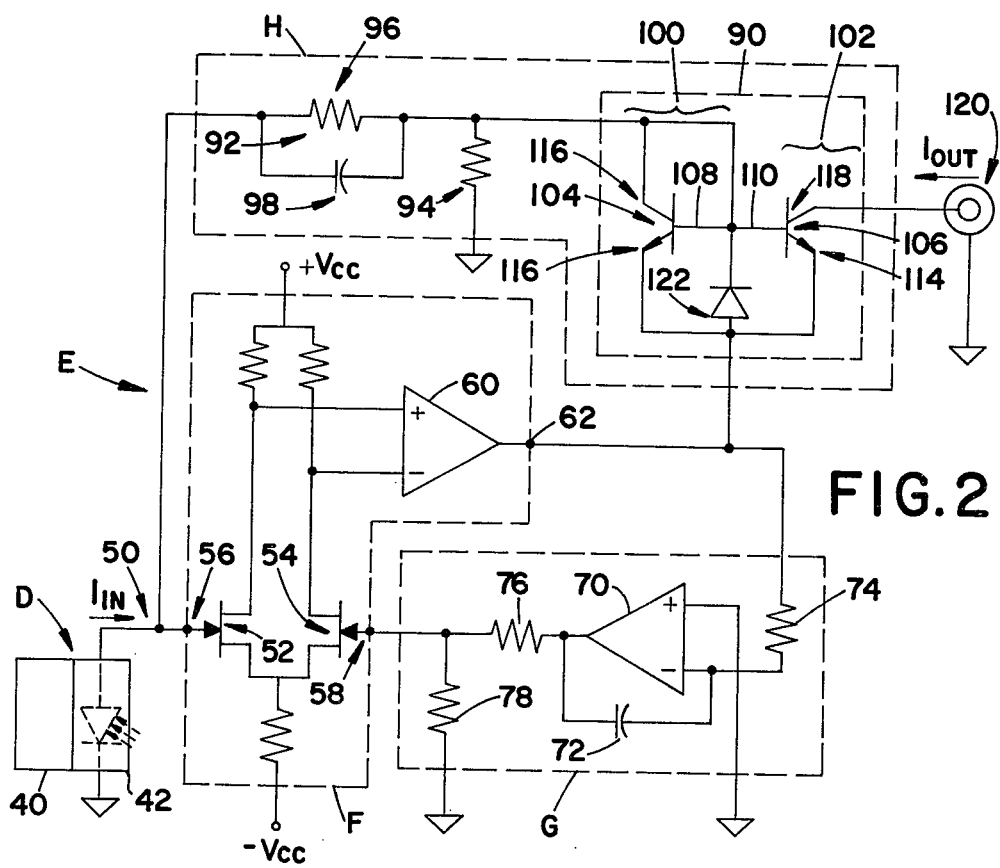

CURRENT AMPLIFIER WITH AUTOMATIC DRIFT CORRECTION FOR TOMOGRAPHIC SCANNERS

BACKGROUND OF THE INVENTION

This application pertains to the art of electrical amplifiers, and more particularly, to a current amplifier with a wide dynamic range and automatic drift correction. The invention is particularly applicable to the amplification of current signals from silicon photodiodes and more specifically, to scintillation crystal photodiode radiation detectors in conjunction with computerized tomographic scanning apparatus. The invention will be described with particular reference to computerized tomography. However, it will be appreciated that the invention has much broader applications such as, electrical meters, measuring devices, and other electrical apparatus that implement current amplification.

Generally, a computerized axial tomographic scanner comprises a source of radiation for irradiating a patient positioned within the scan circle and a plurality of radiation detectors positioned opposite the scan circle from the source of radiation. The origin of the source of radiation is caused to move about the scan circle to irradiate the patient from a plurality of directions. The detectors are positioned and monitored to determine the amount of radiation attenuation along a plurality of known paths crossing the scan circle. With well known computer reconstruction techniques, the radiation attenuation measured along the known paths is reconstructed into an image of the planar region of the patient. The radiation detectors generally comprise a scintillation crystal positioned to recieve the incident radiation and a photomultiplier tube optically coupled with the scintillation crystal. Alternately, ionized gas radiation detectors may be used.

However, photomultiplier tubes are costly, may have a poor time response, lack linearity and reliability, and draw relatively large amounts of power.

Photodiodes have found little acceptance as a replacement for photomultiplier tubes because they produce signals of much lower amplitudes. The low amplitudes create problems with noise and tend to increase the usable dynamic range.

The present invention contemplates a new and improved current amplifier which overcomes all of the above problems and others and provides an amplifier which is low in cost, has a wide, linear dynamic range and a uniforma response.

SUMMARY OF THE INVENTION

In accordance with the present invention, there is provided a computerized tomographic scanning apparatus for examining a planar slice of an object within a scan circle with radiation and for producing a representation of an image of the planar slice. The scanning apparatus comprises a radiation source for producing a generally planar array of radiation, at least one radiation detector for producing electrical signals in response to incident radiation, an amplifier for amplifying the detector signal, and a processing means for processing the representation of an image. The amplifier comprises a first amplifier means operably connected with the radiation detector; and a current mirror means comprising a current receiving section for receiving a current flow from the detector and a current generating means for generating a mirror current proportional to the received current. The current mirror is operatively connected with the first amplifier means. The current receiving section is operatively connected with the radiation detector. The current generating section is connected with the processing means for providing the signals to be processed into the representation.

In accordance with the present invention, there is provided a computerized tomographic scanning apparatus for examining a planar slice of an object within a scan circle with radiation and for producing a representation of an image of the planar slice. The computerized tomographic scanning apparatus comprises a source of radiation for generating a planar array of radiation, at least one radiation detector for producing electrical signals in response to received radiation, a detected signal amplifier for amplifying the signals produced by the radiation detector, and a processing means for producing the representation of an image. The detector signal amplifier comprises a first amplifier means for producing an output voltage in response to the electrical signals. The first amplifier means has a first input operatively connected with the detector, a second input, and a first amplifier means output. The detector signal amplifier further comprises an automatic correction means for providing the second input with a correction voltage for nulling the output voltage when the at least one detector is receiving substantially no radiation. The automatic correction means comprises an integrating amplifier having an input directly connected with the first amplifier means output, an output operatively connected with the second input, and an integrating time constant which is longer than the duration of time which the at least one detector receives radiation from during a normal tomographic scan.

A principal advantage of the invention is that it provides a very wide linear dynamic range.

Another advantage of the present invention is that it corrects automatically without manual adjustment, for temperature and aging induced variations in the offset of the amplifier and the like, all referenced generically as drift correction.

Other advantages of the present invention include low cost, good response time, high reliability, low input impedance, and high output impedance.

BRIEF DESCRIPTION OF THE DRAWINGS

The invention may take physical form in certain parts and arrangement of parts, a preferred embodiment, end of which will be described in detail in this specification and illustrated in the accompanying drawings which form a part hereof.

FIG. 1 is illustrative of the tomographic scanner in accordance with the present invention; and FIG. 2 is illustrative of a current amplifier with automatic correction in accordance with the present invention.

DESCRIPTION OF A PREFERRED EMBODIMENT

The drawings are for the purpose of illustrating preferred embodiments of the invention only and not for purposes of limiting it. With reference to the drawings, FIG. 1 shows a computerized tomographic scanning apparatus A. A rotating fan beam type scanner is illustrated, however, the invention is also applicable to traverse and rotate, eccentric rotational, and other types of scanners. The scanner includes a scan circle B which is adapted to receive a planar region of a patient to be examined. Adjacent the scan circle is a rotatably mounted source of radiation C for irradiating the scan circle with a generally planar fan beam or set of divergent rays of radiation. Disposed opposite the scan circle and the source of radiation are a plurality of radiation detectors D. Connected with each radiation detector D is an amplifier E for amplifying the output signal of the radiation detector.

Looking to FIG. 2, each of the amplifiers E comprises a first amplifier means F for producing an output voltage responsive and corresponding to the amplitude of a received input signal, an automatic correction means G for providing the first amplifier means with a correction voltage which tends to null the output voltage and a feedback loop H connecting the output of the first amplifier means F with the input from detector D. The output of the amplifier E is connected with processing means J of FIG. 1 for reconstructing a tomographic image from the amplified signals from the plurality of detectors.

FIG. 1 illustrates a computerized tomographic scanner in accordance with the present invention. The scanner comprises a tubular element 10 which functions to support a patient 12 or other object in the scan circle B for examination. The source of radiation C is mounted for rotational movement about tubular element 10. The source comprises an x-ray tube 14 and a collimator mechanism 16 for defining the shape of the beam of rays of radiation. The collimator mechanism may be adjustable for selecting different size scan circles and different thicknesses of patient slices for examination. A reference detector 18 measures the intensity of radiation before it traverses the scan circle. A means 20 rotates the source of radiation and provides an indication for the angular orientation of the source relative to the scan circle.

The radiation detectors D take several forms. The detectors may rotate with the source of radiation. In such an embodiment they may only span the arc defined by the maximum fan of radiation. Alternately, the detectors may be stationary as shown in phantom. In such an implementation, they may span the arc defined by end detectors 22 and 24, or they may circumscribe the entire scan circle. The amplifiers E are each connected to one of detectors D. In the preferred embodiment, each detector D and amplifier combination are physically combined in a single physical structure.

The output of the amplifiers is connected to the processing means J which comprises a comparator 26 for comparing the intensity of radiation before and after traversing the scan circle. The comparator provides a processor 28 with a series of indications of the logarithm of the radiation attenuation along various paths through the scan circle. Processor 28 operates on the data with conventional algorithms to produce an electronic representation of the tomographic image for display on a video monitor 30. A suitable processor is described in co-pending application Ser. No. 32,452 filed Apr. 23, 1979, the disclosure of which is incorporated herein by reference.

Details of the preferred embodiment of detector D and amplifier E are illustrated in FIG. 2. The detector D comprises a scintillation crystal 40 such as bismuth germanate and a photodiode 42. The photodiode 42 is optically coupled to the scintillation crystal 40, to produce an output current responsive to light produced by the scintillation crystal. The photodiode and scintillation crystal are covered with a light impermeable material to prevent stray illumination from causing extraneous signals. The photodiode 42 is preferably a silicon photodiode operated in the photovoltaic current mode to provide the widest possible spectrally compatible linear dynamic range. The photodiode current is directly proportional to the intensity of radiation received by the scintillation crystal. Numerous other combinations of scintillation crystals and photodiodes or solid state radiation detectors may be used.

The photodiode current is received by first amplifier means F of current amplifier E. The amplifier input means 50 is connected with a first amplifier means F. The first amplifier means F comprises a first transistor means 52 and a second transistor means 54 which are connected together as a differential amplifier. In the preferred embodiment, the first and second transistor means 52 and 54 are a pair of matched monolithic dual J-FET's e.g, 2N5564. The gate of the first transistor means is operatively connected to a first input 56 of the first amplifier means F. The gate of the second transistor means 54 is operatively connected with a second input 58. The use of a dual J-FET is advantageous because they have very low current and voltage noise, and require a low input bias current. The low noise of the amplifier allows a wide dynamic range of photodiode currents to be amplified without the addition of significant noise from the amplifier.

First and second transistor means 52 and 54 are connected respectively with first and second inputs of an operational amplifier 60, e.g., an LF 353. The operational amplifier subtractively combines the signals from the first and second transistor means to produce on a first amplifier means output 62. Output voltage 62 is a voltage which is related to the difference between the signals received at the first and second inputs. If transistor means 52 and 54 were biased to produce voltages of the opposite polarities, the signals could be combined by operational amplifier 60. Accordingly, in the preferred embodiment, the first amplifier means is a differential amplifier means.

Generally, first amplifier means F would produce a non-zero output voltage, even when the photodiode is dark. This non-zero voltage is attributable to the finite impedance of the photodiode, the input offset voltage, and bias current of the amplifier. Further, this non-zero dark diode voltage is time and temperature dependent. The standard technique of manually adding an offset voltage to null the dark diode voltage becomes inaccurate as FET's age and as their temperature changes. Accordingly, the invention incorporates an automatic continuous drift correction circuit that does not depend on manual adjustments or outside controls.

The automatic drift correction means G comprises an integrating amplifier means directly connected with the output 62 of the first amplifier means F and a voltage divider connecting the integrating amplifier means with the second input of the differential amplifier. The integrating amplifier means comprises an operational amplifier 70, a capacitor 72 and a resistor 74. The operational amplifier may be an LF 353, capacitor 72 may be 1 mf and resistor 74 may be 100 M ohms. The resistor 74 connects an inverting input of operational amplifier 70 with the output 62 of the first amplifier means. A non-inverting input of the operational amplifier is connected with ground. Capacitor 72 is connected in parallel across this input and the output of the operational amplifier. The RC time constant of capacitor 72 and resistor 74 determines the time constant of the integrating amplifier means. The voltage divider comprises a resistor 76 connecting the output of operational amplifier 70 and the second input 58 of the first amplifier means and a resistor 78 connected between resistor 86 and ground. Resistors 76 and 78 may be 10K and 20 ohms, respectively. The effect of the voltage divider is to multiply the time constant of the integrator by the ratio $R_{78}/(R_{78}+R_{76})$.

The time constant is longer than the duration that the scintillation crystal is iradiated during a tomographic scan. This retains the correction signal at essentially the non-irradiated level during a scan. The output voltage at output 62 during a scan is the difference between the irradiated and the non-irradiated voltage. The duration of a scan may be as short as five seconds or less and the interval between scans may be as long as a minute or more.

The output 62 of the first amplifier means F is connected with the feedback loop H. Feedback loop H is a negative feedback loop which connects the first amplifier means output 62 with the first input 56 and forms a virtual ground at the input. Because the photodiode is a current source, the virtual ground at the input of the amplifier is ideally suited as an interface which preserves the diode's linearity over a wide dynamic range. The feedback loop H comprises a mirror current means 90, a first impedance 92 connecting the mirror current means to the amplifier input and a second impedance 94 connecting the mirror current means to the ground. The ground mirror means produces an output or mirror current which is substantially equal or proportional in magnitude but opposite in direction to a received current. In the preferred embodiment, impedance 92 is a parallel connected 20 M resitor, 96 and a 15 pf capacitor 98; impedance 94 is a 20K resistor. The capacitor 98 performs a band limiting function. The ratio of resistances 96 to 94 determines the gain of amplifier E. Current mirror means 90 comprises a current receiving section 100 for receiving a current flow from the input 50 and from a ground across impedance 94 which flows to the first amplifier means output 62. Further, the current mirror means comprises a current generating section 102 for generating a mirror current which is generally equal to the current flowing through the current receiving section 100. In the preferred embodiment, the current receiving and current generating sections of the current mirror means comprise closely matched monolithic NPN transistors 104 and 106, such as a MAT01 transistor pair. Bases 108 and 110 of transistors 104 and 106, respectively are connected together. Emitters 112 and 114 of transistors 104 and 106 are connected to the first amplifier means output 62. Because the transistors are connected base to base, and emitter to emitter, the base-emitter voltage of both transistors will be equal. Accordingly, the collector current of the current generating section 102 will equal the collector current of the current receiving section 100, for closely matched transistors. Collector 116 of the current receiving section is connected with the bases. Collector 118 of the current generating section is connected with output 120 of amplifier E.

A diode 122 is connected between the bases of the current mirror transistors and their emitters to prevent amplifier F from becoming an open loop. Because the input offset voltage of amplifier F can be either polarity, output 62 can likewise be of either polarity. However, transistor 104 only allows current to flow when output 62 is negative. If diode 122 were absent, a negative initial offset voltage would cause amplifier F to perceive an open loop. When the loop is open, the output of amplifier F approaches the positive supply voltage. Under a high positive voltage at output 62, transistors 104 and 106 could undergo reverse breakdown causing permanent damage to the transistors. The diode may be a PAD 50 low leakage diode.

This provides a current in, current out low noise amplifier with a low input impedance and a high output impedance, selectable current gain, and a wide linear dynamic range. Further, the output signal has substantially the same sign and magnitude as a conventionally used photomuliplier tube for tomographic scanners. Thus, a scintillation crystal, photodiode, and amplifier assembly can replace the scintillation crystal and photomultiplier tube assembly on existing scanners without modifying other parts of the scanner or the software for processing the data from the detectors.

Looking now to the operation of amplifier E, when the photodiode is not illuminated, the input offset voltage and bias current to the first amplifier means F would cause a positive or negative output voltage at the output 62 of the first amplifier means. This output voltage would cause an output current. However, this positive or negative voltage causes automatic correction means G to supply a correction voltage to input 58 of amplifier means F. As the correction voltage increases or decreases, the voltage at output 62 decreases or increases until the voltage at 62 reaches zero. This is the steady state condition between tomographic scans. More specifically, the positive or negative voltage at output 62 induces a charge on capacitor 72. This charge, in turn, biases operational amplifier 70 to produce a drift correction voltage. The first amplifier means F subtractively combines a drift correction signal from input 54 with the input offset, thus reducing the first amplifier means output voltage. As long as the amplifier means voltage is non-zero, the charge on capacitor 72 is increased or decreased and the drift correction signal increased or decreased. Accordingly, a steady state condition is achieved in which the drift correction signal nulls the output of the first amplifier means. When the first amplifier means output is zero, there is substantially no current flow through the feedback loop and the output current is substantially zero.

When the detector D is irradiated, the scintillation crystal produces light. The light in turn causes the photodiode to generate a current I, $I_{in}$ the amplitude of which is directly related to the intensity of radiation irradiating the detector. In a tomographic scanner, each detector is irradiated for a relatively short duration at relatively long intervals. Commonly, a detector is irradiated for a couple of seconds during each scan and scans are spaced by a minute or more. During the scan, the intensity of radiation striking each detector commonly varies as radiation intensity along different paths through the object are sampled. The different intensities along the different paths cause a varying photodiode current.

The photodiode current causes the first amplifier means F to produce a negative output voltage at output 62. The RC time constant of resistor 74 and capacitor 72 is long compared with the duration for which the detector is irradiated. This retains the drift correction signal at input 58 generally constant during a scan. Accordingly, the first amplifier means output voltage is corrected for the input offset voltage by the automatic correction circuit. However, the automatic correction circuit is designed to be too slow to null or reduce significantly the first amplifier means output voltage attributable to the photodiode current during a scan.

The photodiode current induced negative output voltage from the first amplifier means causes a current flow through the feedback loop. A current from the amplifier input through resistor 96 holds the amplifier input virtually to ground. A current from ground through resistor 94 is added with the current through resistor 96. The current sum flows through the current receiving section 100 of the current mirror means to the output 62 of the first amplifier means. The current generating section 102 produces an output current equal in magnitude to the current flowing through the current input section.

The output voltage at 62 of the first amplifier means, $V_0$, is balanced by the sum of the base-emitter voltage of the received section 100, $V_{be}$, and the voltage across resistor 94, $V_{94}$, i.e.;

$$V_0 = V_{be} + V_{94}$$

in which, $$V_{be} = \frac{KT}{q} \ln\left(\frac{I_{out}}{I_s} + 1\right)$$

where,
K = Boltzmann's constant
T = Temperature in °K.
q = charge of an electron
$I_s$ = Reverse saturation current of the transistor
alternately stated, $$V_0 = V_{be} + I_{94} R_{94}$$

Because the input to the amplifier is a virtual ground, the voltage across resistor 96 is essentially equal to the voltage across resistor 94, i.e.;

$$I_{in} R_{96} = I_{94} R_{94}$$

The output current is equal to the sum of the currents through resistors 94 and 96 but with the opposite sign, i.e.;

$$I_{out} = -(I_{in} + I_{94}) = -\left(1 \frac{R_{96}}{R_{94}}\right) I_{in}$$

Accordingly, the gain is:

$$\text{Gain} = -\left(1 + \frac{R_{96}}{R_{94}}\right)$$

The preferred embodiment may be modified in numerous ways without departing from the invention. For example, J-FET's 52 and 54 may be eliminated if low noise and low input bias currents are not required or if an operational amplifier with suitable specifications is available. If the low input impedance is to be retained, operational amplifier 60 may similarly be replaced with an operational amplifier having a low input impedance. If the sign of the drift correction output were reversed, it could be additively combined with the other input to operational amplifier 60. A delay means may supplement or replace capacitor 72 and resistor 74. PNP transistors can be used in the current mirror means with the appropriate alterations in the other components to reverse positive and negative polarities. The current mirror can be altered to generate an output current which is proportional or inversely proportional to the received current. Obviously, further modifications and alterations will occur to others upon reading and understanding this specification. It is my intention to include all such modifications and alterations which come within the scope of the following claims or their equivalents.

I claim:

1. A computerized tomographic scanning apparatus for examining a planar slice of an object within a scan circle with radiation and producing a representation of an image of the planar slice comprising:
   a source of radiation for producing a generally planar array of radiation;
   at least one radiation detector for producing electrical signals in response to received radiation from the source;
   a current amplifier comprising a first amplifier means having a first input operatively connected with said detector, and a current mirror means comprising a current receiving section for receiving current signals and a current generating section for generating a mirror current proportional to the current signals received by the current receiving section, said current mirror means operatively connected with said first amplifier means and said current receiving section being operatively connected with said first input; and
   processing means for producing the representation of an image, said processing means being operatively connected with said current generating section.

2. The apparatus as set forth in claim 1 further comprising a first impedance operatively connecting said current receiving section with said first input and a second impedance operatively connecting said current receiving section with a reference potential.

3. The apparatus as set forth in claim 2 wherein said first amplifier means has a second first amplifier means input and wherein said first amplifier means is a differential amplifier means for subtractively combining signals received on the first and second inputs to produce a difference signal on the first amplifier means output.

4. The apparatus as set forth in claim 3 further comprising an automatic correction means for producing a correction voltage, said automatic correction means having an input connected with an output of the first amplifier means and having an output on which the correction voltage is produced, the output of the automatic correction means being connected with the second input whereby the correction voltage tends to alter the first amplifier means output voltage.

5. The apparatus as set forth in claim 4 wherein said automatic correction means comprises an integrating amplifier having an integrating time constant, said integrating amplifier causing the correction voltage to tend to null the first amplifier means output voltage delayed by generally the integrating time constant.

6. A computerized tomographic scanning apparatus for examining a planar slice of an object within a scan circle with radiation and producing a representation of an image of the planar slice comprising:

a radiation source for producing a generally planar array of radiation;

at least one radiation detector for producing electrical signals in response to received radiation from the source which has traversed the scan circle;

a detector signal amplifier operatively connected with said at least one radiation detector comprising a first amplifier means for producing an output voltage in response to said electrical signals, said first amplifier means having a first input operatively connected with said at least one detector, a second input, and a first amplifier means output on which the output voltage is produced; an automatic drift correction means for providing said second input with a correction voltage for nulling said output voltage when said at least one detector is receiving substantially no radiation, said automatic correction means comprising an integrating amplifier means having at least one integrating amplifier input directly connected with said first amplifier means output and an integrating output operatively connected with said second input, said integrating amplifier means having an integrating time constant which is longer than the duration of time which the at least one detector receives radiation during a normal tomographic scan; and processing means for producing the representation of an image, said processing means being operatively connected with each amplifier detector signal amplifier.

7. The apparatus as set forth in claim 6 further comprising a feedback loop operatively connected with said first amplifier means output and said first input.

8. The apparatus as set forth in claim 7 wherein said feedback loop comprises a current mirror means serially connected with a first impedance, and a second impedance operatively connected between said current mirror means and a reference potential source.

9. The apparatus as set forth in claim 8 wherein said current mirror means comprises a current receiving section for receiving a current flow and a current generating section for generating a mirror current proportional to the current signals received by the current receiving section, said current receiving section being operatively connected with said first and second impedences, whereby the potential differences between said first input, the reference potential source and the first amplifier means output induces the current flow received by the current receiving section.

10. The apparatus as set forth in either of claims 1 or 9 wherein said current receiving section comprises a first transistor means and said current generating means comprises a second transistor means, said first and second transistor means having electrically coupled bases.

11. The apparatus as set forth in claim 10 wherein said first and second transistor means are matched first and second NPN transistors, and wherein said first and second transistors have emitters operatively connected together, said first NPN transistor has a collector operatively connected with said first and second impedances and said bases and said second NPN transistor has a collector operatively connected with said amplifier output.

12. The apparatus as set forth in either one of claims 1 or 6 wherein said at least one detector comprises a scintillator crystal optically coupled with a photodiode whereby the electrical signals produced by the detector are photodiode currents whose amplitude varies with the intensity of radiation received by the scintillation crystal.

13. The apparatus as set forth in claim 6 wherein said integrating amplifier means comprises an operational amplifier having first and second operational amplifier inputs and an operational amplifier output, a capacitive means operatively connected with said first operational amplifier output, said second operational amplifier input operatively connected with a reference potential, a first resistive means directly connected with said first operational amplifier input and said first amplifier means output, whereby the integrating time constant is a function of the RC time constant of said capactive and resistive means.

14. The apparatus as set forth in either one of claims 1 or 6 wherein said first amplifier means comprises a first field effect transistor having a gate operatively connected with said first input, a source, and a drain, a second field effect transistor having a gate, a source, and a drain, and an operational amplifier having an inverting input operatively connected with the source of one of said field effect transistors, a non-inverting input operatively connected with the source of the other of said field effect transistors and an output operatively connected with said first amplifier means output, whereby said first amplifier means functions as a differential amplifier.

15. The apparatus as set forth in claim 13 wherein said automatic correction means further comprises a voltage divider operatively connected with said operational amplifier output and said second input.

* * * * *